United States Patent [19]

Dukes et al.

[11] 4,227,079

[45] Oct. 7, 1980

[54] MULTIPATH FINE POSITIONING BEAM DIRECTOR

[75] Inventors: John N. Dukes, Los Altos Hills; Charles E. Bryson, III, Palo Alto; Lynn Weber, Saratoga, all of Calif.

[73] Assignee: Hewlett-Packard Company, Palo Alto, Calif.

[21] Appl. No.: 969,758

[22] Filed: Dec. 15, 1978

[51] Int. Cl.[2] .......................... G01D 5/34; G01J 3/42
[52] U.S. Cl. ............................ 250/231 SE; 356/319; 356/326; 350/6.91
[58] Field of Search ............... 250/231 SE, 234, 235, 250/236; 356/319, 321, 326, 328; 350/6.5, 6.91, 6.9, 6.1, 6.6

[56] References Cited

U.S. PATENT DOCUMENTS

| 2,705,434 | 4/1955 | Hansen | 325/326 X |
| 3,520,625 | 7/1970 | Gillieron et al. | 250/234 X |
| 3,765,742 | 10/1973 | Walles | 350/6.1 |
| 3,859,617 | 1/1975 | Oka et al. | 250/211 K X |
| 3,892,961 | 7/1975 | Bachmann | 250/211 K |

Primary Examiner—David C. Nelms
Assistant Examiner—Edward P. Westin
Attorney, Agent, or Firm—Ronald E. Grubman; John A. Frazzini

[57] ABSTRACT

A beam directing device is provided which employs one or more mirrors mounted on a single rotatable shaft. The orientation of the shaft controls the rotational orientation of these directing mirror(s) to direct the beam toward any of a number of sample or reference cells. Behind each cell is a cube corner which reflects the beam back to the directing mirror(s) for reflection toward the detector. In one embodiment, a shaft encoded senses the orientation of the shaft, the encoder output being servoed against a position signal to coarsely rotate the shaft in order to direct the beam to a sample cell and thence to a spectrograph slit. A pair of slit diodes detect the beam overlap on each side of the slit and their output is used to accurately position the beam on the slit to within one second of arc and correct for deviations in beam direction.

6 Claims, 4 Drawing Figures

MULTIPATH FINE POSITIONING BEAM DIRECTOR

BACKGROUND OF THE INVENTION

The invention is concerned generally with optical beam directing devices and more particularly with a beam director for a spectrograph. Typically, a spectrograph employs a beam chopper to direct the beam alternately through a sample cell and a reference cell. A typical chopper, shown in FIG. 1, employs a pair of stationary mirrors 15 and 16 at opposite corners of a rectangle and a pair of mirrors 12 and 17 mounted perpendicular to rotating shafts at the other two corners. The rotating mirrors 12 and 17 are semicircular so that during half of each rotation, the mirrors direct a beam 11 along a path 13 through a sample cell 133 at the top of the rectangle and for the other half of each rotation, the beam is directed along a path 14 through a reference cell 134 on the bottom of the rectangle. In some devices, a number of sample cells can be successively rotated into the spectrograph beam by a carousel. Vibrations from the mechanical motion of the mirrors and carousel or misalignment of the sample cells can generate small deviations in the beam direction which limit the accuracy of the spectrograph. Since the spectrograph's grating produces an image of the slit on a detector array, a detector in the array must be as large as the image. To accomodate a large number of detectors, it is necessary to use a narrow slit and narrow beam. The spectrograph is thus sensitive to deviations in beam direction so that the spectrograph accuracy can be increased by use of a beam directing system that adjusts for deviations in beam direction.

SUMMARY OF THE INVENTION

In accordance with the illustrated preferred embodiment for directing a spectrograph beam, the present invention provides a pair of directing mirrors mounted on and parallel to the axis of a common rotatable shaft. The shaft can be rotated to change the angle of incidence of the beam on the directing mirrors to reflect the beam toward any of several sample or reference cells. The rotational position of the directing mirrors can be detected by a shaft encoder empolying an optical analog transducer. The range of shaft rotation is divided into a number of addresses which are used in the coarse rotations of the shaft.

Fine positioning is provided by a servo mechanism from a pair of diodes which detect the beam overlap on each side of the slit. In this embodiment, control of the shaft orientation to within one second of arc is possible, enabling precise correction for beam deviations due to such things as variations in sample cell alignment and beam misalignment due to external influences such as air currents and structural vibrations. Insertion of the sample cells therefore requires less care and time than in present devices.

DESCRIPTION OF THE PREFERRED EMBODIMENT

Figure 1:
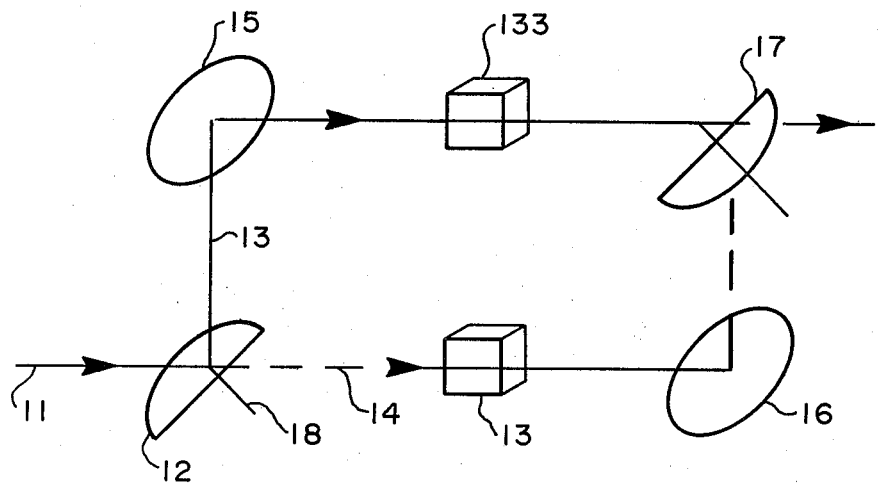
FIG. 1 illustrates the structure of a typical beam chopper.
Figure 3:
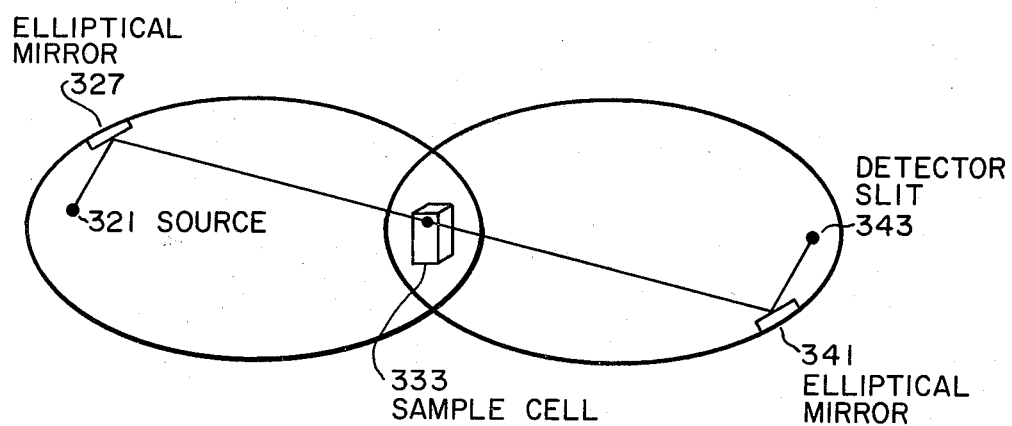
FIG. 3 illustrates the role of the elliptical mirrors.
Figure 2:
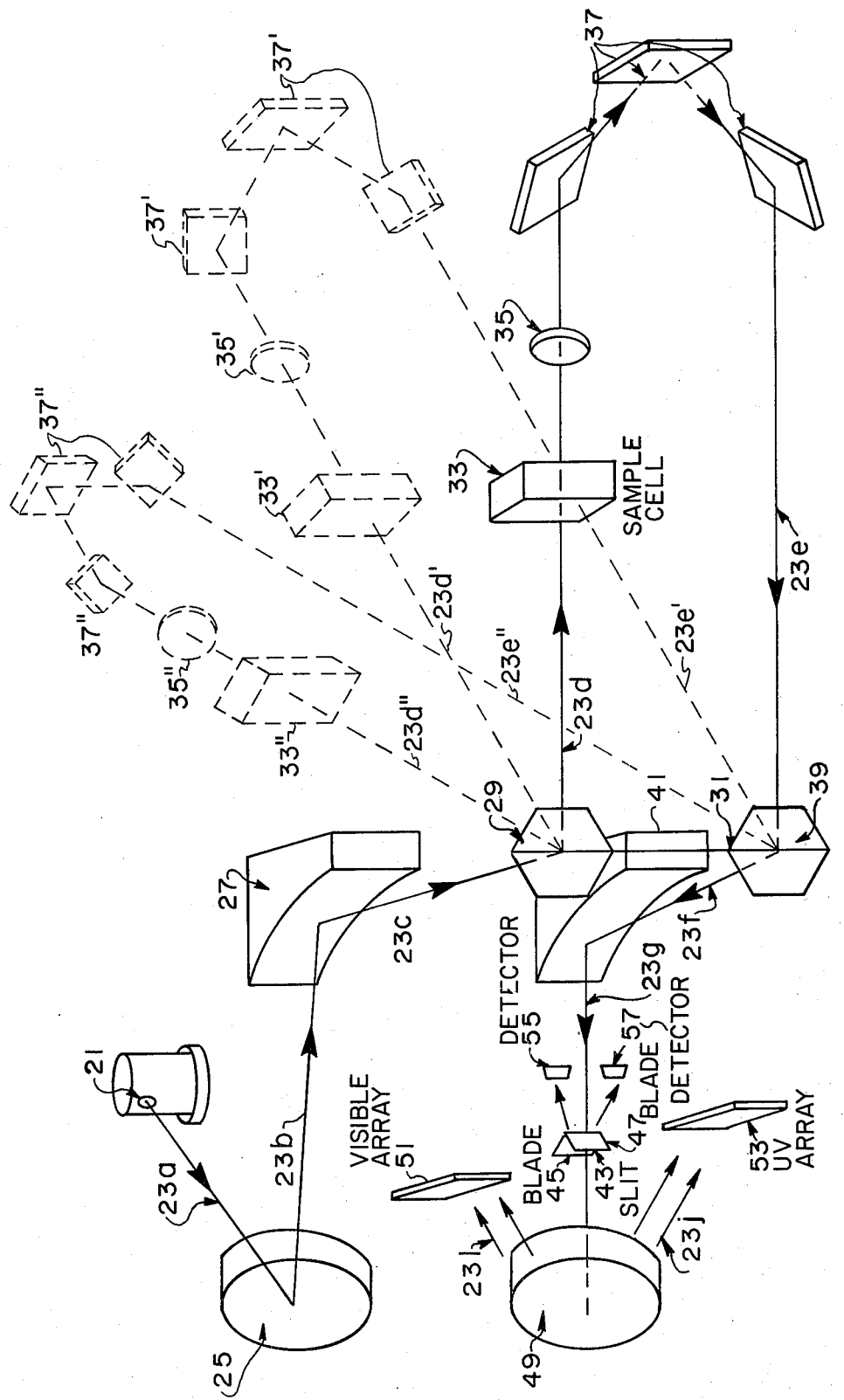
FIG. 2 is a diagram of a beam path in a preferred embodiment of the beam director in a spectrograph.

In FIG. 2 there is shown a beam path 23 in a preferred embodiment of a beam director in a spectrograph. The beam is emitted through a source lamp slit 21 to a source mirror 25 which reflects it to an elliptical mirror 27. Elliptical mirrors 27 and 41 are positioned in the beam path to focus the light first on a sample cell 33 and then again onto a detector slit 43. (This process is illustrated in FIG. 3 where the beam is emitted by a source 321 to an elliptical mirror 327 which focusses it on a sample cell 333. The beam passes through sample cell 333 to a second elliptical mirror 341 which focusses it on a detector slit 343.)

The beam reflects off mirror 27 to a reflecting means which is mounted on a single rotatable element. In this embodiment, the reflecting means is a pair of mirrors 29 and 39 mounted on and parallel to the rotatable element, which is a shaft 31. Shaft 31 can be rotated so that mirror 29 reflects the incident beam 23c along any of numerous sample paths, typically labelled 23d, to a preselected sample position. Corresponding to each position is a sample cell, a field lens, and a folding element typically labelled 33, 35, and 37 respectively. It is convenient to use a cube corner for the folding element so that the beam returns along path 23e parallel to path 23d. The path is thus "folded" back to the reflecting means, enabling the second rotatable mirror 39 to be mounted on the same shaft as mirror 29. The use of a single rotatable element simplifies machine movement and eliminates errors which arise when more than one rotating element is used as in the beam chopper described above.

Because mirrors 29 and 39 are parallel and paths 23d and 23e are parallel, the beam will reflect off mirror 39 along a path 23f which is parallel to path 23c. The beam is now imaged by elliptical mirror 41 onto slit 43 through which part of the beam, e.g. 50%, passes and is dispersed by a spectral dispersing element, such a holographic grating 49, to a visible light detector array 51 and a UV detector array 53. In one preferred embodiment, slit 43 is formed by a pair of reflective blades 45 and 47 which reflect the overlap of the beam on each side of the slit to a pair of detectors 55 and 57 for use in the fine positioning of shaft 31 to adjust the shaft's rotational orientation to equalize the output of detector 55 and detector 57.

Figure 4:
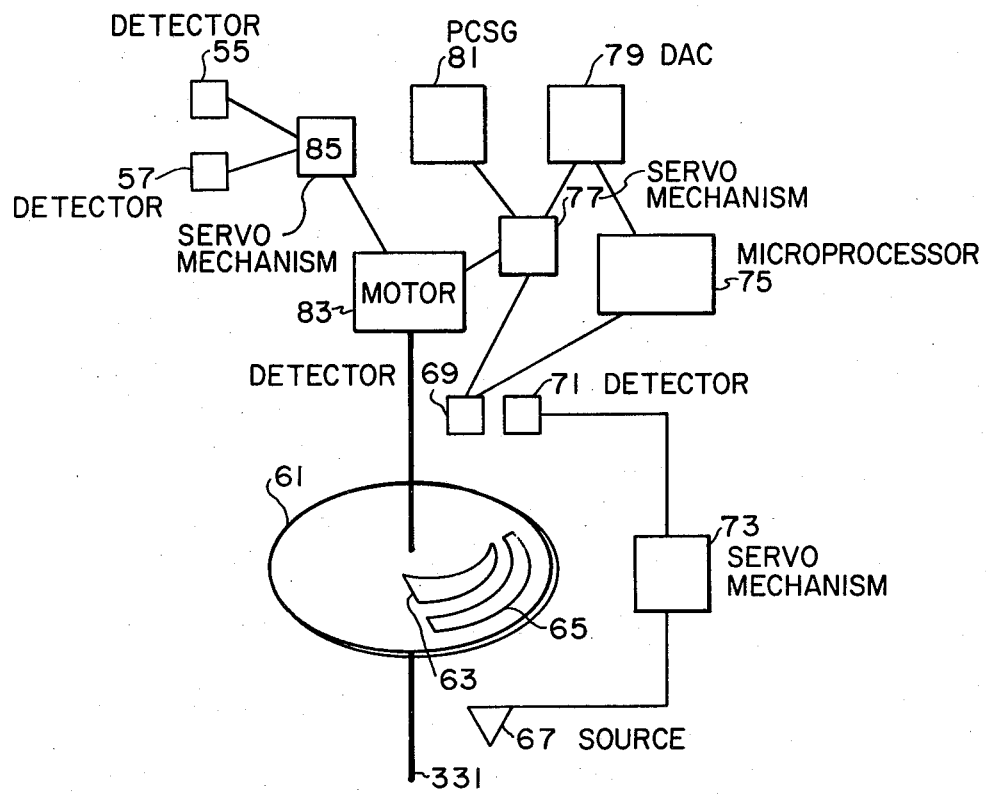
FIG. 4 shows a control means and sensing means for regulating the shaft's rotational orientation.

The rotational orientation of the shaft is sensed by a sensing means which in one preferred embodiment is a shaft encoder employing an optical analog transducer illustrated in FIG. 4. The transducer includes a disc 61 in which are placed circumferentially a pair of slots 63 and 65 which allow light from a source 67 below the disc to fall on a pair of detectors 69 and 71 respectively. The width of slot 63 varies so that the intensity of light reaching detector 69 varies with orientation of the shaft. The output from detector 69 thus indicates the rotational orientation of the shaft. Slit 65 is of uniform width and allows light to reach detector 71. The output from detector 71 is sent to a servo mechanism 73 for control of source 67 to maintain a constant intensity of light on detector 71.

The shaft encoder output is used by the control means to regulate the rotational orientation of the shaft. Shaft rotation is produced by a motor 83 which is controlled by the output from a servo mechanism 77. The servo mechanism output represents the difference between the shaft encoder output and the signal from either a Digital to Analog Converter (DAC) 79 or a Position Command Signal Generator (PCSG) 81. The coarse rotational orientations of the shaft are listed as addresses which, in one embodiment, are eleven bit numbers in a microprocessor 75. The first three bits contain the sample position which sets the beam direction within an angular span containing the given sample. The size of the span is determined by the dimensions of the spectrograph and cube corners and in one embodiment is 12°. The remaining eight bits control the coarse rotational orientation within this span to within two minutes of arc. For a preselected address, the microprocessor makes the DAC 79 generate a signal which represents the desired rotational orientation of the shaft. This signal is compared in servo mechanism 77 with the shaft encoder signal and the difference between them is used to control motor 83.

When the spectrograph is turned on, a search mode is implemented to find the address of each sample. The beam is set at the edge of a given sample span and the address is repeatedly incremented until the beam falls on slit 43. This address is stored as the sample address and the procedure is repeated in each sample span.

In a move between addresses, PCSG 81 generates a signal for comparison in servo mechanism 77 with the shaft encoder output. The variation of this signal with time is such as to rotate the shaft between addresses in the least time. If the beam misses the slit after the coarse rotation then the search mode is implemented to find that sample address again. If the coarse rotation lands the beam on the slit diodes then the fine positioning system takes over. The output of diodes 55 and 57 are subtracted in servo mechanism 85 and its output adjusts the shaft rotation to center the beam on slit 43. These small rotations change the position where the beam strikes the cube corner and this varies the lateral distance between beam paths 23d and 23e. This shift also shifts path 23g sideways to fine position the beam on the slit. The sample address is automatically updated if the fine rotation shifts the beam within another coarse address.

The beam can thus be directed to a number of sample positions as illustrated in FIG. 2 by the dashed lines and the system can compensate for beam shifts due to various causes such as sample cell misalignment. The correction of beam direction by the rotatable mirrors and the use of cube corner folding means relieves the need in this device for precision maintenance or operation procedures. The reduction of mechanical motion reduces machine vibration. This reduction and the active correction of beam position allow more accurate measurement of the beam.

We claim:

1. Apparatus for directing a beam in an optical instrument along a plurality of sample paths and for correcting deviations in beam direction, comprising:
   reflecting means rotatably mounted along a single rotation axis for directing the beam along any preselected sample path;
   a plurality of folding elements, each element associated with a sample path for folding the path back to the reflecting means;
   sensing means for sensing the rotational orientation of the reflecting means; and
   control means, responsive to signals from the sensing means, for controlling the rotation orientation of the reflecting means.

2. Apparatus as in claim 1 wherein the folding element is a cube corner.

3. Apparatus as in claim 2, in which the sensing means is a shaft encoder employing an optical analog transducer comprising;
   a disc mounted perpendicular to the rotation axis of the reflecting means, having a pair of circumferential slots through the disc, the first slot of increasing width and the second slot of constant width;
   a light source adjacent to the slots for emission of light through both slots;
   a first detector, responsive to light which has passed through the first slot, to generate a first signal representing the rotational orientation of the reflecting means;
   a second detector, responsive to the light which has passed through the second slot, to generate a second signal; and
   a first servo mechanism, responsive to the second signal to regulate the light source to maintain a constant illumination of the second detector.

4. Apparatus as recited in claim 1 wherein the control means comprises:
   a microprocessor to store addresses corresponding to rotational orientations of the reflecting means;
   a Digital to Analog Converter responsive to said microprocessor to generate a first position signal corresponding to a selected address;
   a second servo mechanism, responsive to the difference between the first position signal and the signal from the sensing means, to produce a first control signal;
   a motor responsive to the first control signal to rotate the reflecting means;
   said microprocessor at turn-on initiating a search mode which locates the address corresponding to each sample path; and
   said microprocessor responding to user commands to select the address corresponding to a selected sample path.

5. Apparatus as in claim 4 further comprising a Position Command Signal Generator responsive to said microprocessor producing a second position signal for use in rotating the reflecting means between two selected orientations, said second position signal varying in time in a manner which, within control means parameters, will minimize the time to perform the rotation, said second servo mechanism being responsive during a period of rotation to the difference between the second position signal and the signal from the sensing means.

6. Apparatus as in claim 1 further comprising:
   a pair of reflecting blades disposed to form a slit located along the output path;
   a slit detector associated with each blade for generating a signal proportional to the part of the beam reflected from its associated blade; and
   a third servo mechanism, responsive to the signals from the slit detectors, which generates a second control signal for use by the motor to fine position the beam on the slit.

* * * * *